United States Patent [19]
DeSatnick et al.

[11] Patent Number: 4,733,662
[45] Date of Patent: Mar. 29, 1988

[54] TISSUE GRIPPING AND CUTTING ASSEMBLY FOR SURGICAL INSTRUMENT

[75] Inventors: Allen H. DeSatnick, Marblehead; Herbert D. Marcus, Winchester; Paul A. Torrie, Marblehead, all of Mass.

[73] Assignee: Minnesota Mining and Manufacturing Company, St. Paul, Minn.

[21] Appl. No.: 4,650

[22] Filed: Jan. 20, 1987

[51] Int. Cl.[4] ............................................. A61B 17/32
[52] U.S. Cl. .................................... 128/305; 128/751; 30/162
[58] Field of Search ............... 128/305, 312, 311, 318, 128/751, 754, 755; 30/151, 162, 152

[56] References Cited

U.S. PATENT DOCUMENTS

| | | | |
|---|---|---|---|
| 1,339,692 | 5/1920 | Diamant . | |
| 2,131,780 | 10/1938 | Storz | 128/309 |
| 2,258,287 | 10/1941 | Grieshaber | 128/309 |
| 2,843,128 | 7/1958 | Storz | 128/309 |
| 3,835,859 | 9/1974 | Roberts et al. | 128/305 |
| 3,929,123 | 12/1975 | Jamshidi | 128/754 |
| 4,067,340 | 1/1978 | Le Noir | 128/305 |
| 4,396,021 | 8/1983 | Baumgartner | 128/754 |
| 4,491,132 | 1/1985 | Aikins | 128/305 |
| 4,523,379 | 6/1985 | Osterhout et al. | 30/151 |
| 4,600,014 | 7/1986 | Beraha | 128/754 |

FOREIGN PATENT DOCUMENTS 853410 3/1940 France .

Primary Examiner—Dalton L. Truluck
Assistant Examiner—Denise Whelton
Attorney, Agent, or Firm—Donald M. Sell; James A. Smith; Robert W. Hoke, II

[57] ABSTRACT

A surgical instrument including a reusable handle and a removable sheathed blade assembly comprising an elongate sheath with a plurality of elongate surgical blades longitudinally received within said sheath and selectively projectable therefrom along guided paths for exposure of the working heads of the blades. The working heads define, respectively, a cutting head and a gripping head. The sheathed assembly is introduced an operating site whereat the gripping head is exposed and engaged with tissue to be cut. The cutting head is subsequently moved into cutting engagement with the gripped tissue, after which both blades are retracted into the sheath and the sheathed blades removed from the operating site. The cutting blade is directly manually reciprocated with the gripping blade engaged with the cutting blade through a connection which allows for reciprocation of the gripping blade in response to reciprocal movement of the cutting blade, or, alternatively, reciprocation of the cutting blade independent of the gripping blade.

9 Claims, 8 Drawing Figures

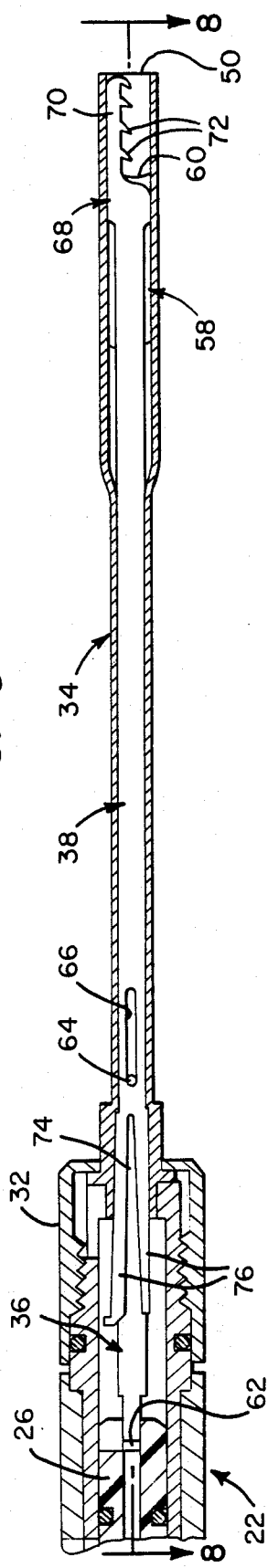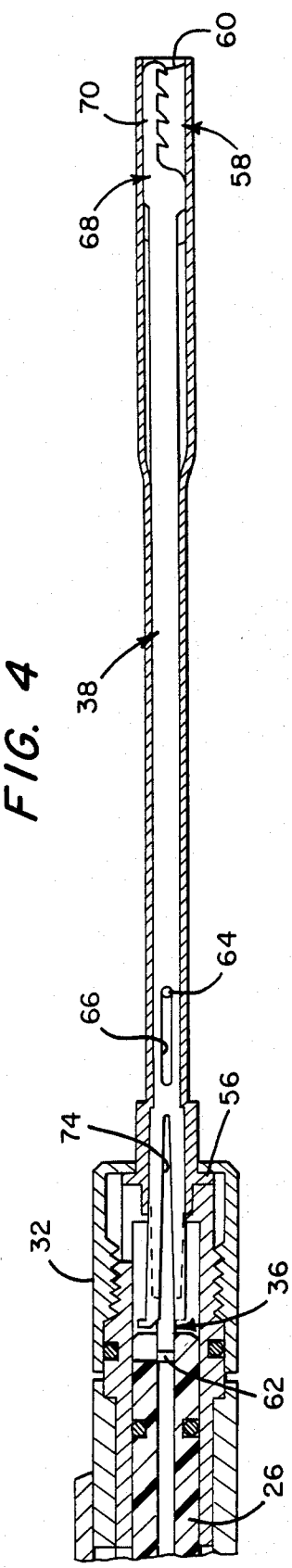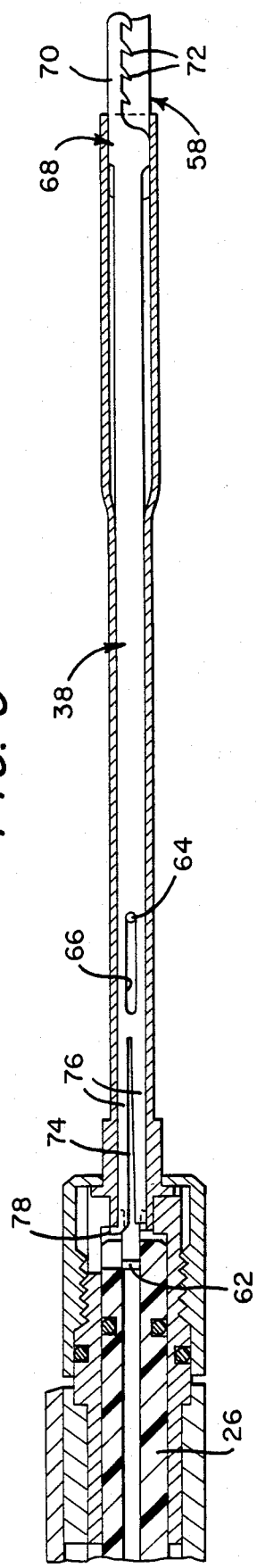

TISSUE GRIPPING AND CUTTING ASSEMBLY FOR SURGICAL INSTRUMENT

BACKGROUND OF THE INVENTION

The present invention is broadly directed to surgical instruments, and more specifically to instruments useful in arthroscopic surgery and similar surgical procedures wherein access to the surgical site is limited and/or difficult.

The surgical environment of the invention normally involves performance of surgical procedures through small incisions through which the instruments are introduced and subsequently manipulated. With the use of surgical cutting instruments, for example cutting blades, substantial care must be taken not only in the cutting manipulation thereof, but also in the actual introduction of the cutting blade to the cutting site and the subsequent removal therefrom.

A problem associated with the cutting manipulation of surgical cutting instruments is the difficulty in stabilizing the tissue as the tissue is cut. This is particularly the case wherein use of a single instrument is desired or required for minimal body invasion and/or trauma.

As noted in substantial detail in Aikens, U.S. Pat. No. 4,491,132, issued Jan. 1, 1985, one known procedure for the atraumatic introduction of a cutting instrument utilizes a protective sheath. The sheath, a linear hollow member, has the blade completely received and sheathed therein. The blade remains in the sheath until the distal or forward end of the sheath is positioned proximate the site of use. At that time, the blade is mechanically extended from the sheath, either by an actual extension of the blade from the sheath or by a corresponding retraction of the sheath relative to the blade. The Aikens patent notes the desirability for such instruments and discloses selected variations thereof.

The necessity for surgical procedures in limited access environments has also led to the development of instruments incorporating means for guiding a cutting blade or the like during the actual use thereof at the cutting site. Such known means include opposed guides or tracks along which the blade travels during the cutting operation. In this regard, note the following:

| Roberts et al | U.S. Pat. No. 3,835,859 | Sept. 1, 1974 |
| Le Noir | U.S. Pat. No. 4,067,340 | Jan. 10, 1978 |

The instruments of both Roberts et al and Le Noir are rather cumbersome, requiring the use of separate handles to adjust and position the guide and subsequently manipulate the blade.

Copending application Ser. No. 780,895, Allen H. DeSatnick, filed Sept. 27, 1985, now patent number commonly owned with the present application, discloses a sheath and blade assembly. The sheath functions both as a bladeenclosing protective means and as a blade guide during surgical cutting. The sheath and blade assembly are removably mountable on a reusable handle incorporating an actuation mechanism for manipulation of the blade relative to the sheath utilizing a single slide button. The disclosure of the DeSatnick application, Ser. No. 780,895, is herein incorporated by reference.

SUMMARY OF THE INVENTION

The surgical instrument of the present invention includes a reusable handle and a sheath-protected blade assembly wherein the sheath, in addition to its protective function also acts to both guide and direct received blades along common preselected paths, either straight or laterally curving.

The invention itself is primarily concerned with a blade assembly which uniquely provides for a holding or gripping of tissue during the actual cutting procedure, utilizing a single instrument with a single manipulable control thereon. As such, the instrument is particularly adapted to be held and manipulated by one hand. Further, by incorporating both the tissue stabilizing means and the tissue cutting means on the single instrument, only the one instrument need be introduced to the operating site, providing atraumatic benefits including reduced trauma, less cluttered operating site, and the like.

The actual gripping and cutting procedure is effected by a blade assembly comprising a minimum of two blades, a cutting blade and a gripping blade. The blade assembly is received within the sheath with the working ends of the blades selectively extensible beyond the leading tip of the sheath, along parallel guide paths determined by the sheath, for engagement with the tissue at the operating site. The sheath itself provides an effective means for introducing the enclosed blade assembly to the operating site after which the leading working ends of the blades are exposed for use in the surgical procedure.

The sheath and blade assembly are removably mounted on a reuseable handle which is basically the handle disclosed in DeSatnick application. Both the sheath and the cutting blade, at the proximal or near ends thereof engaged with the handle, are similarly configured in the manner of the sheath and cutting blade of the DeSatnick application and similarly engage the handle for manipulation thereby. The blade assembly of the present invention differs by the incorporation therein of a gripping blade which is slidably guided within the sheath parallel to and immediately adjacent the cutting blade. The cutting blade is manipulated from the reusable handle through a single slide button thereon. A lost-motion connection is provided between the cutting blade and the gripping blade for a selective manipulation of the gripping blade in conjunction with the cutting blade, thus providing for a one-hand control of both blades.

In order to allow for selective stabilization of the gripping blade in the extended gripping position thereof, the gripping blade, at the proximal end thereof, is configured for a frictional engagement with the sheath upon full extension of the gripping blade. In this manner, provision is made for a locking of the gripping blade in its extended position while the cutting blade, through the lost-motion connection, is manipulable relative thereto both for an initial retraction of the cutting blade to fully expose the gripping head of the gripping blade for engagement with the tissue and for the subsequent manipulation of the cutting blade relative to the gripping blade to effect the tissue severing.

With regard to the specific components, the sheath is an elongate tubular member of a sufficient internal diameter to accomodate the blades, preferably two, of the blade assembly. The proximal end portion of the sheath is configured to releasably mount within the reusable handle. The distal or leading end portion of the sheath will normally be slightly enlarged to accomodate the enlarged blade heads or working ends. The sheath, as illustrated, is of a linear tubular configuration throughout the full length thereof. Alternatively, the leading or distal end portion of the sheath, as a specialized guide means, can be laterally curved away from the longitudinal axis of the sheath and, as noted in the DeSatnick application, can be flattened to acheive particular advantages including maximum resistance to blade rotation, reduced size, etc.

The sheath is of a length so as to completely receive the leading or working ends of the blades therein upon a retraction of the blades relative to the sheath. Both blades, as is conventional in surgical metal blades, are capable of a slight degree of resilient flexing to appropriately interact with the sheath and the guiding function perfomed thereby. Both the blades include enlarged leading or working end portions with the cutting blade having a forwardly directed cutting tip and the gripping blade having a series of longitudinally extending laterally inwardly directed gripping teeth.

The near or proximal end of the cutting blade includes a laterally directed tab which engages within the internal slider of the handle for manipulation through the single slide button. At a point along the cutting blade forward of the proximal end thereof, the cutting blade is provided with a laterally directed pin. This pin engages within a longitudinally elongate slot in the adjacent gripping blade. The pin and slot relationship allows for a free travel of the cutting blade relative to the gripping blade until engagement of the pin with either of the opposed ends of the slot. Upon engagement with either slot end, and a continued manipulation of the cutting blade through the handle slider, a corresponding movement of the gripping blade will be effected.

The near or proximal end portion of the gripping blade is bifurcated or slotted to define a pair of rearwardly extending slightly diverging integral fingers which, toward the extreme proximal end, define a blade width greater that the internal diameter of the sheath. Thus, as the gripping blade is forwardly extended through manipulation of the cutting blade, a progressively greater frictional engagement is effected between the proximal end portion of the gripping blade and the sheath. In this manner, the gripping blade will automatically releasable lock in its forwardy extended position allowing for both a free retraction of the cutting blade within the limits of the pin and slot association, and a stabilization of the gripping blade relative to the handle for a manipulation of the working end of the gripping blade into engagement with the tissue to be cut or severed. An appropriate laterally directed lug is provided at the extreme end of one of the gripping blade fingers for engagement with the corresponding end of the sheath, thereby defining a forward limit to the extension of the gripping blade.

In actual use, the handle-mounted sheath, with the blades retracted therein, will be introduced to the operating site, for example a chamber within the knee. Through a one-hand manipulation of the cutting blade, both blades, guided by the sheath, will be extended to the forward limit of the gripping blade. At that point the gripping blade is frictionally fixed in its extended portion within the sheath. The cutting blade is then retracted independently of the gripping blade and the instrument manipulated to engage the gripping head of the gripping blade with the tissue, for example the meniscus to be cut or severed. With the tissue firmly gripped, the cutting blade is again advanced to effect the desired cutting. The advancing blade is again guided by the sheath with the actual path of the cut defined by the position of the gripping head in the tissue. The cutting blade is then retracted and the gripping blade disengaged from the tissue and also retracted into the sheath. The instrument can then be safely removed from the operating site. As noted in the DeSatnick application, the sheath is particularly adapted for accomodating fluid flow at the site, for either aspirating or irrigating purposes. Appropriate controls for the fluid flow are incorporated within the reuseable handle itself.

BRIEF DESCRIPTION OF THE DRAWINGS

FIG. 3 is an enlarged longitudinal cross-sectional view illustrating both blades in their fully retracted position within the sheath;

FIG. 4 is a view similar to FIG. 3 with the working heads of the blades aligned within the sheath preparatory to a simultaneous extension of both blades;

FIG. 5 is a view similar to FIG. 4 with both blades in their fully extended position and with the gripping blade, at the following end proximal to the handle, frictionally locked within the sheath;

DESCRIPTION OF PREFERRED EMBODIMENT

Figure 1:
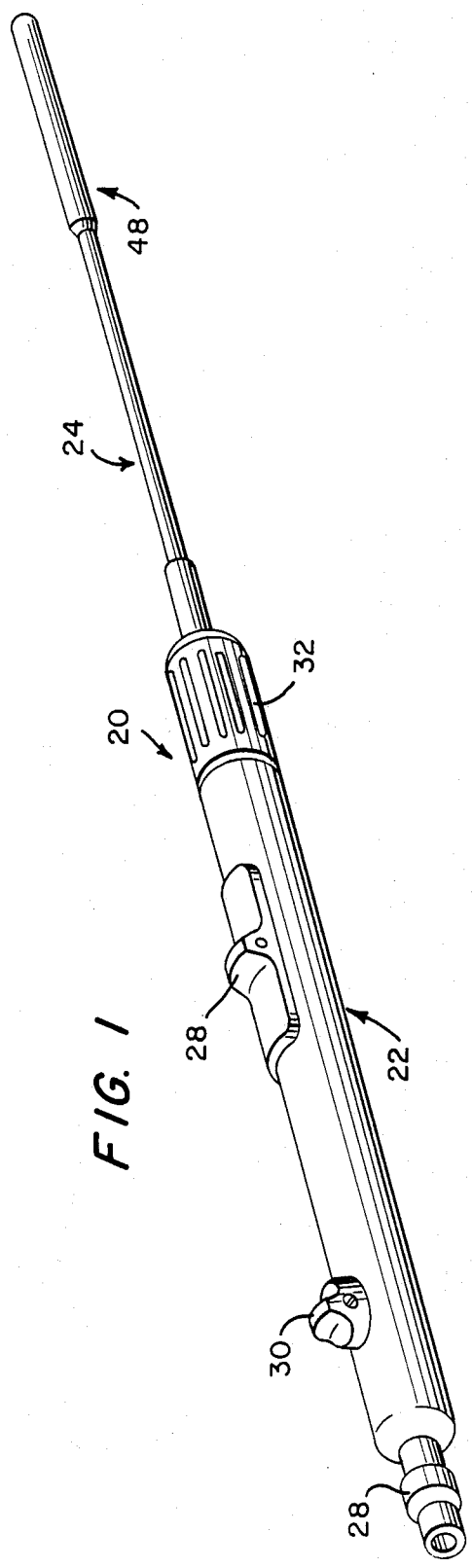
FIG. 1 is a perspective view of the surgical instrument of the present invention.
Figure 2:
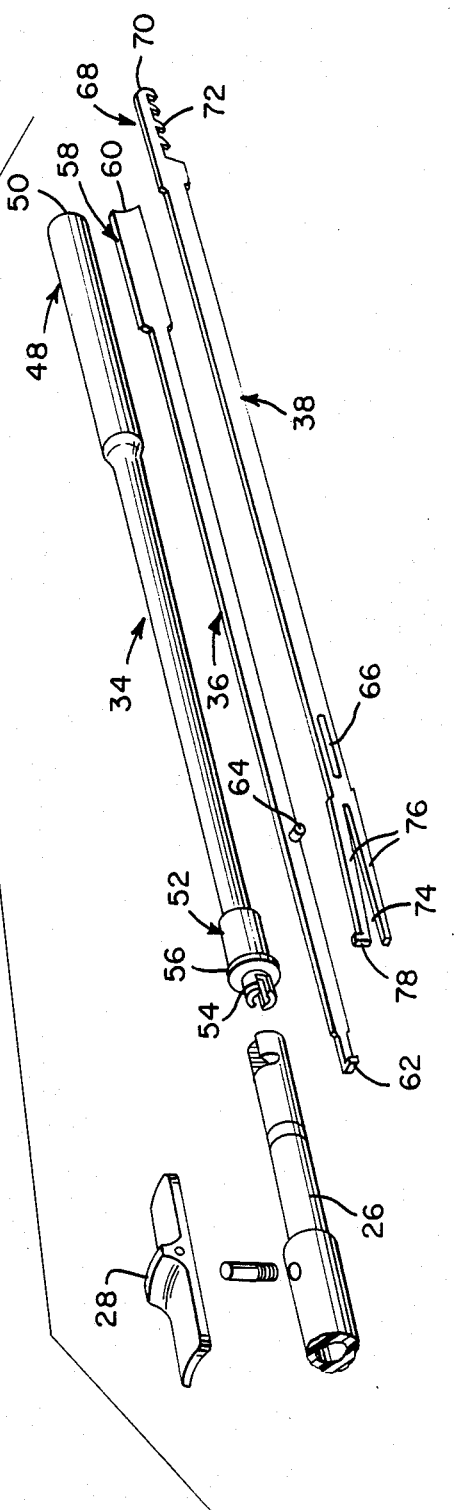
FIG. 2 is an exploded perspective view of the components of the invention.

Referring now more specifically to the drawings, reference number 20 designates a surgical instrument in accord with the present invention. The instrument includes two basic modules, a reusable handle 22 and a disposable or replacable sheath and blade assembly 24.

The handle 22 is basically as disclosed in the copending DeSatnick application, and includes an internal slider 26 controlled by a single finger manipulable external slide button 28. The handle 22 will preferably comprise an elongate cylindrical body for ease of grasping and manipulation with one hand. The body can also incorporate appropriate fluid flow control means 28 and 30 providing for appropriate aspirating/irrigating functions as desired. The handle is also provided, at the leading end thereof, with a retaining cap 32 for a mounting of the sheath and blade assembly 24.

The sheath and blade assembly comprises a sheath 34 and plural blades including a cutting blade 36 and a gripping blade 38. The sheath 34 is of an elongate hollow tubular configuration with a diametrically enlarged extended distal or leading end portion 48 terminating in an open end 50. The near or proximal end portion 52 of the sheath 34 includes rearwardly directed positioning slots 54 and an annular positioning collar 56 immediately forward of the slots 54. This end portion 52 is engaged within the leading end of the handle 22 inward of the retaining cap 32 in manner generally indicated in FIGS. 3–8 and more specifically detailed in the DeSatnick application. The leading end portion 48 of the sheath 34 has been illustrated as a linear tubular continuation of the main body of the sheath inward thereof. However, as desired, this leading end portion may be laterally curved relative to the longitudinal axis of the sheath and may be flattened to achieve selected advantages, including maximum resistance to rotation of the blades slidably guided therethrough.

The cutting blade 36 is an elongate flat member of an appropriate surgical metal including a transversly enlarged elongate leading end or working head 58 having an appropriate cutting tip or edge 60 thereon. The near or following end portion of the blade 36 includes a laterally directed tab 62 which engages within the internal slider 26 of the handle 22 whereby longitudinal manipulation of the slider 26 effects a direct corresponding longitudinal manipulation of the cutting blade 36 within the sheath 34. The cutting blade 36 is completed by the provision of a laterally directed pin 64 fixed to an intermediate portion of the cutting blade 36 forward of the near end thereof.

The gripping blade 38 is, similar to the cutting blade 36, of a flat elongate configuration formed of appropriate surgical metal, and is of a length slightly less than that of the cutting blade 36. The gripping blade 38 is juxtaposed the cutting blade 36 within the sheath 34 with the pin 64 engaged through a longitudinally elongate slot 66 in the gripping blade to define therewith what might be considered a "lost-motion" connection between the blades.

The leading or working end portion of the blade 38 includes a gripping head 68 in the nature of an elongate integral finger or extension 70 of a substantially reduced transverse width relative to that of the leading end portion This extension, in the illustrated embodiment, includes a plurality of longitudinally spaced rearwardly inclined gripping teeth 72 generally directed inward of the extension 70 toward the longitudinal center line of the blade 38 and terminating within the lateral confines of the full width of the blade 38.

The near or following end portion of the gripping blade 38 includes a rearwardly opening longitudinally extending elongate slot 74 defining a pair of elongate blade sections 76 integrally formed with the blade 38 and rearwardly diverging at a slight degree relative to each other for a progressive increase in the transverse width of the gripping blade 38 as the rear end of the blade is approached. The widths of the cutting blade 36, and the blade 38 forward of the diverging sections 76, closely approximate that of the internal diameter of the corresponding portions of the sheath 34 whereby desired blade guidance is provided in conjunction with a free sliding movement of the blades within the sheath. The progressive diverging of the sections 76, either one relative to the other or both relative to the longitudinal center line of the gripping blade 38, is such as to increase the width of the following or near end portion of the gripping blade 38 beyond that of the rear portion of the sheath 34 whereby progressive forward movement of the gripping blade 38 will effect a frictional engagement of the end portion thereof, and more particularly the sections 76, within the rear portion of the sheath 34. The inherent resiliently flexible nature of the material of the blade 38 will result in a spring-resisted inward compressing of the sections 76 toward each other as they are progressively received within the sheath. It is believed this relationship will be readily appreciated from FIGS. 3-5 of the drawings. In order to limit forward extension of the gripping blade 38 relative to the sheath, at least one of the sections 76 is provided with a laterally directed lug or tab 78 on the extreme rear end thereof, this tab engaging against the inner end on the sheath 34 and defining a proper positioning of the gripping blade for use at the operation site.

As will be noted, the elongate pin-receiving slot 66 is provided through the gripping blade 38 immediately forward of the bifurcated rear end portion of the blade 38.

FIGS. 3-7 illustrate the sheath and blades assembled in operative position and mounted on the handle. These figures also sequentually illustrate the positions of the blades relative to each other during use of the surgical instrument.

In FIG. 3, the blades 36 and 38 are in their innermost of rearwardmost position with the cutting blade 36 retracted by a rearward movement of the internal handle slider 26 through a rearward sliding of the finger-controlled button 28. This full rearward movement of the cutting blade 36 engages the pin 64 thereon with the rear end of the slot 64 of the gripping blade 38 and effects a corresponding rearward retraction of blade 38. In this position, as will be appeciated, the leading or working ends of both blades are fully retracted into the protective enclosure of the sheath, and the sheath and blade assembly are adapted for introduction to the operation site. Once the leading portion of the sheath and blade assembly is positioned at the operation site, for example a knee cavity, the internal slider of the handle 22 is, through a finger manipulation of the slide button 28, forwardly extended to forwardly move the engaged cutting blade 36. This forward movement of the cutting blade 36 is, initially, effected independently of the gripping blade 38 as the pin 60 moves forwardly along the slot 66. Upon engagement of the pin with the forward end of the slot, the leading ends of the blades 36 and 38 come into substantial alignment immediately within the forward end of the sheath. Continued forward movement of the cutting blade 36 results in a simultaneous forward movement of the gripping blade 38 and a projection of both blades beyond the protective sheath as in FIG. 5.

As the projecting blades approach the forwardmost limit thereof, the rear portion of the gripping blade 38, through the spread "spring" sections 76 integrally defined thereon, frictionally engages within the rear portion of the sheath, with the forward movement of the gripping blade 38 limited by engagement of the laterally directed lug 78 thereon with the rear end edge of the sheath 34. Upon a completion of the forward projection of the gripping blade 38, and a releasable frictional locking of this blade to the sheath in its forwardmost position, the cutting blade 36, again through a finger manipulation of the slide button and internal handle slider 26, is retracted within the sheath with the pin 64 moving freely rearward within the slot 66 and with the gripping blade 38 stabilized by the spring-biased engagement of the rear sections 76 with the sheath. In retracting the cutting blade 36 relative to the forwardly fixed gripping blade 38, the cutting blade 36 is retracted only sufficiently to move the leading cutting end thereof into the sheath for a full exposure of the gripping head 68 of the gripping blade. In this position, the pin 64 will normally seat at the inner end of the slot 66.

Figure 6:
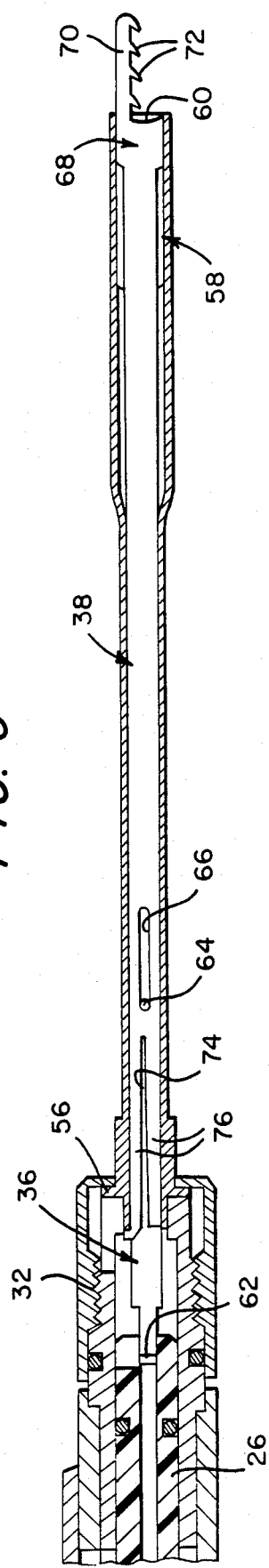
FIG. 6 is a view similar to FIG. 5 with the cutting blade retracted relative to the forwardly fixed gripping blade.
Figure 7:
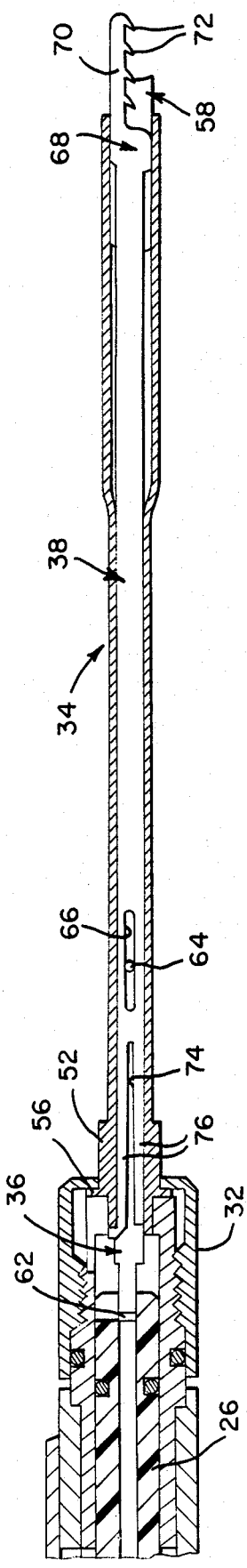
FIG. 7 is a view similar to FIG. 6 illustrating forward movement of the cutting blade relative to the fixed gripping blade.
Figure 8:
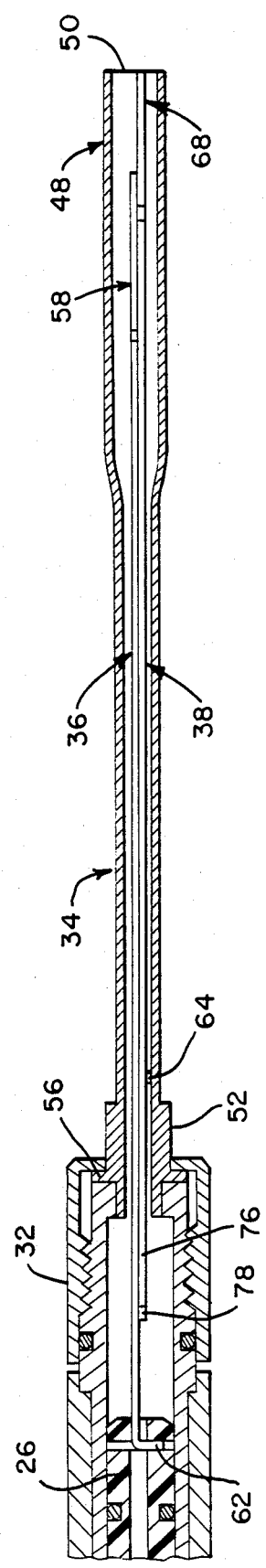
FIG. 8 is a longitudinal section taken substantially on a plane passing along line 8—8 in FIG. 3.

The instrument, as now presented in FIG. 6 with only the gripping head 68 exposed, is manually manipulated through the handle 22 to engage the gripping head, and more particularly the teeth 72, with the tissue, for example the meniscus, to be stabilized or gripped during the cutting procedure. Once the tissue is properly engaged, the cutting blade, again through a manipulation of the internal slider 26 by the external finger-controlled button 28, is forwardly projected to cut or sever the gripped tissue stabilized by the gripping head 68 immediately adjacent the cutting site. The actual path of the working head of the cutting blade, because of the relationship of the blades, will be indicated by the position of the gripping blade in the tissue. After the cut is completed, the cutting blade is retracted away from the gripping head, the gripping head, through a manipulation of the instrument, is disengaged from the tissue and both blades are retracted into the sheath through a continued rearward drawing of the cutting blade. Once the blades are again both retracted within the sheath, the sheath is removed from the operating site. As will be appreciated, at any time during the use of the instrument, such aspiration or irrigation procedures as may be desired can be performed utilizing the sheath as a fluid conduit.

We claim:

1. In a surgical instrument for use in surgical procedures involving tissue cutting, a sheathed blade assembly comprising an elongate sheath and a plurality of elongate surgical blades longitudinally received within said sheath for reciprocal guided movement therein, said blades comprises a cutting blade and a gripping blade, said gripping blade including a leading end with a working head having gripping means thereon for gripping engagement with tissue, said cutting blade including a leading end with a working head having cutting means thereon for the cutting of tissue engaged by said gripping means, said sheath having forward and rear end portions, said forward end portion terminating in an open forward blade-passing end, each said blade working head being completely retractable into said sheath, positioning means external of said sheath for reciprocation of said blades relative to said sheath and selective extension and retraction of the working head of each blade relative to the open forward end of the sheath for a selective exposure of the working heads of said blades beyond said forward end, means for selectively retaining said gripping blade with the working head thereof exposed beyond the forward end of the sheath independently of said cutting blade, said blades including following end portions extending rearward of said sheath, said blade following end portions, upon reciprocation of said blades, being selectively extensible forwardly into the sheath and retractable rearwardly from the sheath, said means for retaining said gripping blade with the working head thereof exposed being defined by a laterally enlargement of the following end portion of said gripping blade, said sheath having a generally constant internal transverse dimension along at least the rear end portion thereof, said lateral enlargement defining a transverse blade dimension greater than said internal transverse dimension of the rear end portion of the sheath whereby extension of the following end portion of the gripping blade into the sheath will effect a releasable frictional fixing of said gripping blade within said sheath, the lateral enlargement of the following end portion of the gripping blade being defined by a pair of rearwardly extending elongate sections, at least one of said sections diverging laterally outward from the other section and incorporating a degree of resilient flexiblity for a selective lateral flexing of said one section toward the other section upon extension of said sections into the sheath, means limiting the forward extension of the following end portion of the gripping blade in to the sheath, and blade control means engaged between said cutting blade and said gripping blade for a selective reciprocation of said gripping blade in response to reciprocation of said cutting blade, said positioning means external of said sheath for reciprocation of said blades being engaged solely with said cutting blade.

2. The surgical instrument of claim 1 wherein said blade control means comprises a lateral projection on said cutting blade extending transversely toward said gripping blade, and an elongate slot defined longitudinally along said gripping blade and receiving said projection, said slot having closed longitudinally opposed ends defining abutments for said projection whereby engagement of said projection with either abutment, and movement of the projection in the direction of the engaged abutment, will effect a corresponding movement of the gripping blade, said projection being freely longitudinally movable within said slot between said abutments independent of a corresponding movement of said gripping blade.

3. The surgical instrument of claim 2 wherein said blades are flat and positioned in immediately adjacent parallel planes.

4. The surgical instrument of claim 3 wherein said working head on said gripping blade comprises an integral forwardly projecting elongate extension, said extension including plural gripping teeth extending therefrom and rearwardly inclined relative to the leading end of the gripping blade.

5. In a surgical instrument for use in surgical procedures involving tissue cutting, a sheathed blade assembly comprising an elongate sheath and a plurality of elongate surgical blades longitudinally received with said sheath for reciprocal guided movement therein, said blades comprising a cutting blade and a gripping blade, said gripping blade including a leading end with a working head having gripping means thereon for gripping engagement with tissue, said cutting blade including a leading end with a working head having cutting means thereon for the cutting of tissue engaged by said gripping means, said sheath having forward and rear end portions, said forward end portion terminating in an open forward blade-passing end, each said blade working head being completely retractable into said sheath, positioning means external of said sheath for reciprocation of said blades relative to said sheath and selective extension and retraction of the working head of each blade relative to the open forward end of the sheath for a selective exposure of the working heads of said blades beyond said forward end, and blade control means engaged between said cutting blade and said gripping blade for a selective reciprocation of said gripping blade in response to reciprocation of said cutting blade, said positioning means external of said sheath for reciprocation of said blades being engaged solely with said cutting blade.

6. The surgical instrument of claim 5 wherein said blade control means comprises a lateral projection on said cutting blade extending tranversly toward said gripping blade, and an elongate slot defined longitudinally along said gripping blade and receiving said projection, said slot having closed longitudinally opposed ends defining abutments for said projection whereby engagement of said projection with either abutment, and movement of the projection in the direction of the engaged abutment, will effect a corresponding movement of the gripping blade, said projection being freely longitudinally movable within said slot between said abutments independent of a corresponding movement of said gripping blade.

7. In a surgicnal instrument for use in surgical procedures involving tissue cutting, a sheathed bladed asembly comprising an elongate sheath and a plurality of elongate surgical blades longitudinally received within said sheath for reciprocal guided movement therein, said blades comprising a cutting blade and a gripping blade, said gripping blade including a leading end with a working head having gripping means thereon for gripping engagement with tissue, said cutting blade including a leading end with a working head having cutting means thereon for the cutting of tissue engaged by said gripping means, said sheath having forward and rear end portions, said forward end portion terminating in an open forward blade-passing end, each said blade working head being completely retractable into said sheath, positioning means external of said sheath for reciprocation of said blades relative to said sheath and selective extension and retraction of the working head of each blade relative to the open forward end of the sheath for a selective exposure of the working heads of said blades beyond said forward end, and an elongate handle having a forward end portion including mounting means receiving and releasable mounting the rear end portion of said sheath, said blades including following end portions received within said handle, said positioning means for reciprocation of said blades comprising a slider element within said handle engaged with the following end portion of said cutting blade, and means engaged between said blades selectively engaging said cutting blade with said gripping blade for a reciprocal movement of said gripping blade in response to reciprocation of said cutting blade.

8. In a surgical instrument, a blade assembly including a pair of generally coextensive juxtaposed elongate flat blades comprising a cutting blade and a gripping blade, said gripping blade having a leading end with a working head thereon including gripping means for gripping engagement with body tissue, said cutting blade having a leading end with a working head thereon including cutting means for cutting tissue engaged by said gripping means, manually actuatable positioning means engaged with said cutting blade for a linear reciprocation thereof, and blade control means engaged between said cutting blade and said gripping blade for a selective reciprocal movement of said gripping blade in response to reciprocation of said cutting blade beyond predetermined limits, said cutting blade being freely reciprocal relative to said gripping blade within said predetermined limits.

9. The surgical instrument of claim 8 Wherein said blade control means comprises a lateral projection on said cutting blade extending tranversly toward said gripping blade, and an elongate slot defined longitudinally along said gripping blade and receiving said projection, said slot having closed longitudinally opposed ends defining abutments for said projection whereby engagement of said projection with either abutment, and movment of the projection in the direction of the engaged abutment, will effect a corresponding movement of the gripping blade, said projection being freely movable within said slot between said abutments independent of a corresponding movement of said gripping blade.

* * * * *